United States Patent [19]
Jiang et al.

[11] Patent Number: 5,337,614
[45] Date of Patent: Aug. 16, 1994

[54] FIXTURE FOR TESTING MOUNTING INTEGRITY OF HEAT SINKS ON SEMICONDUCTOR PACKAGES, AND METHOD OF TESTING

[75] Inventors: Xin H. Jiang, Newark; Scott Kirkman, San Jose, both of Calif.

[73] Assignee: LSI Logic Corporation, Milpitas, Calif.

[21] Appl. No.: 935,692

[22] Filed: Aug. 20, 1992

[51] Int. Cl.⁵ .............................................. G01N 3/10
[52] U.S. Cl. ........................................ 73/827; 73/833
[58] Field of Search .................. 73/826, 827, 831–834; 269/87, 91, 165, 172, 203, 216, 218, 219, 257, 289 R

[56] References Cited

U.S. PATENT DOCUMENTS

| | | | |
|---|---|---|---|
| 1,008,926 | 11/1911 | Saylor | 269/218 |
| 2,428,111 | 9/1947 | Eldrup | 269/165 |
| 2,821,080 | 1/1958 | Gemignani | 73/827 |
| 3,159,127 | 12/1964 | Wheeler | 269/165 |
| 3,690,160 | 9/1972 | Kriesten | 73/831 |
| 4,292,852 | 10/1981 | Morris | 73/827 |
| 4,489,363 | 12/1984 | Goldberg | 301/383 |
| 4,876,896 | 10/1989 | Snow et al. | 73/827 |
| 4,895,028 | 1/1990 | Mayer | 73/827 |

FOREIGN PATENT DOCUMENTS 0215046 8/1989 Japan ................................ 73/827

Primary Examiner—Robert Raevis
Attorney, Agent, or Firm—Gerald E. Linden

[57] ABSTRACT

A reliable, repeatable, well-characterized, safe technique for testing the mounting integrity of heat sinks adhered to semiconductor packages is disclosed. Generally, a semiconductor package is secured in a tensiometer, the heat sink is clamped and secured to the spindle of the tensiometer, and a stud-pull type test is conducted.

11 Claims, 4 Drawing Sheets

FIXTURE FOR TESTING MOUNTING INTEGRITY OF HEAT SINKS ON SEMICONDUCTOR PACKAGES, AND METHOD OF TESTING

TECHNICAL FIELD OF THE INVENTION

The invention relates to packaging semiconductor devices and, more particularly, to packages of the type having a heat sink adhesively mounted to the package body.

BACKGROUND OF THE INVENTION

In order to handle and connect a semiconductor die (integrated circuit device) to external systems, it is generally necessary to package the die. This usually involves mounting the die to some sort of substrate, leadframe or carrier, connecting bond pads on the die to some sort of conductive lines or traces and forming a package body around the die. The conductive lines or traces exit the package body, and usually terminate in external leads or pins.

For example, ceramic packages have a package body with a central opening (cavity) in one face for receiving the die, and lead fingers embedded in the body and extending into the opening. The die is connected (usually wire bonded) to the exposed (in the opening) portions of the lead fingers. The lead fingers are connected (internally in the package) to pins exiting a planar surface of the package. These pins are typically arranged in a rectangular (e.g., square) array ("pin grid array"). In some instances, the die-receiving cavity is "up", on one face of the package body, and the pins are on the other, opposite face of the package body. In other instances, the die-receiving cavity is "down", on the same face of the package as the pins (in which case there are no pins in the area of the cavity). (The pins are deemed to be on the "bottom" of the ceramic body.)

Heat is inevitably generated during operation of a semiconductor device, and may become destructive of the device if left unabated. Therefore, it is generally well known to provide some sort of heat sink for such devices. Generally, heat sinks take one of two forms. They may be integral with the device package or they may be external to the device package. In either case, heat sinks generally include a thermal mass in intimate heat conductive relationship to the semiconductor device, and may involve air convection or forced air cooling of the thermal mass.

External heat sinks are mounted in some manner, such as with an adhesive (e.g., silver epoxy), to the semiconductor package which may be provided with thermal slugs and the like to ensure that heat is transferred from the semiconductor die (device) to the heat sink. Evidently, if the heat sink were to become unadhered, and fall off of the package, during subsequent operation of the device, the device would be likely to become overheated and fail. This is entirely unacceptable.

Hence, it is known to test the integrity of the heat sink mount, to ensure that the heat sink remains securely mounted to the semiconductor package throughout the useful lifetime of the semiconductor device.

FIG. 1A shows a typical, cavity-down, ceramic, pin grid array semiconductor package 100, with an external heat sink adhered thereto. A semiconductor die (not visible) is contained within a ceramic package body 102. Pins 104 extend from the bottom 102b of the body. A cavity (not visible) is provided on the bottom of the body for receiving the die. The top surface 102a of the package body is essentially a flat planar surface. Thermal plugs 106 may be provided extending into the package body from the top surface to a die attach pad (not visible) within the package body to which the die is mounted, to ensure a good thermal path from the die to the top (exterior) surface of the package body. More particularly, there is a "heat sink receiving" area 108 (shown as dashed lines) defined on the top surface of the package, and the thermal plugs (if any) would be located within this area. The heat sink receiving area is flush with the top surface of the package, and is intended to receive a heat sink.

An external heat sink 110 is provided (shown spaced apart from the package body, and in cross-section). The heat sink is typically a generally cylindrical structure, having a number of disc-like radially-extending fins 112 spaced along its axis, and a flat bottom surface 110b. Notably, there is a gap (space) 114 between adjacent fins 112. An adhesive (not shown) is provided between the flat bottom surface 110b of the heat sink and the heat sink receiving area of the package body. The heat sink is assembled to the area 108 of the package with the adhesive. The type and amount of adhesive, curing techniques, and the like, are critical process parameters affecting the ultimate structural integrity of the heat sink mount.

FIG. 1B shows another type of semiconductor package 100', such as a plastic package, wherein the top surface 120a of the package body 120 is provided with a thermally-conductive slug 126 extending above the top surface 120a and defining the heat sink receiving area (compare 108). A heat sink, such as the heat sink 110 would be adhered to the top surface 126a of the slug 126.

FIG. 2A illustrates a prior art technique 200 for testing the mounting integrity of a heat sink, such as the heat sink 110 of FIG. 1A. (The technique is equally applicable to the packages of FIGS. 1A and 1B.) A "generic" package body 202 has a heat sink 210 mounted by a thin layer of adhesive 216 to the top surface of the package body. (Pins, and the like, are omitted from the view for illustrative clarity.) The heat sink 210 is placed in a recessed fixture (not shown), and a shear force indicated by an arrow 220 is applied to the package body along an axis 222. This may be done manually by an operator, with a torque wrench adapted to grasp the package body and apply a shearing force between the heat sink and the package body. This method has proven to be manually difficult to perform, to yield inconsistent and un-precise results, and can present a danger to the operator. (When the adhesive bond between the heat sink and the package body fails, there is a sudden "release" of components in close proximity to the operator.) Moreover, this method is only suitable for use with relatively large heat sinks.

FIG. 2B illustrates another technique 200' for testing the mounting integrity of a heat sink on a semiconductor package. In this case, the package body is held by hand, and the tip 232 of a torque wrench 230, is inserted by the operator between the heat sink and the package. The operator manually applies a force, indicated by the arrow 220', sufficient to separate the heat sink from the body (or vice-versa). This suffers from many of the disadvantages of the torque wrench method 200. Also this method is only useful for one type of heat sink.

What is needed is a reliable, safe, quantifiable technique for characterizing the mounting integrity of the adhesive bond between a heat sink and a semiconductor package body.

DISCLOSURE OF THE INVENTION

It is an object of the present invent ion to provide an improved technique for testing the tensile adhesion of heat sinks to semiconductor packages.

It is further object of the present invention to provide a technique for testing the tensile adhesion of heat sinks that is more automatic and precise than prior art techniques.

It is further object of the present invention to provide a technique for testing the tensile adhesion of heat sinks that yields more detailed information (stress.strain curve, maximum load, break load, etc.) than the prior art techniques.

It is a further object of the present invention to provide a technique for testing the tensile adhesion of heat sinks that is easier to perform, safer and more reliable than prior art techniques, and that can be used to test a wide variety of heat sink/package combinations. Furthermore, the present invention has an object of providing a method of testing adhesion which is not necessarily destructive.

According to the invention, a tensile "stud pull" type test is applied to heat sinks mounted externally to semiconductor packages. A special fixture is provided for a suitable test apparatus, such as the INSTRON 4501, computer controlled, tensile tester.

According to an aspect of the invention, the fixture includes:

two braces, each having a flat surface for resting atop a top surface of a semiconductor package body; and two flat, plate-like jaws, each having a semicircular cutout extending from an inner edge thereof, for fitting underneath a fin of a heat sink adhered to the top surface of the semiconductor package body.

According to a feature of the invention, the fixture further includes:

an elongated slot in each of the flat surfaces of the braces, for allowing chip capacitors mounted to the top surface of the semiconductor package to pass freely through the flat surfaces of the braces, thereby ensuring contact between the flat surfaces and the top surface of the semiconductor package body.

According to a feature of the invention, the fixture further includes:

a rod adapted to be secured to the spindle of a tensiometer;

two parallel, spaced-apart, blocks, each block associated with a respective jaw mounted to a respective one of the blocks;

a threaded shaft extending from the one block to the other block, and passing freely through the rod, for adjusting the spacing of the blocks.

According to a feature of the invention, the fixture further includes:

at least one guide rod extending from the one block to the other block, for ensuring that the blocks remain parallel when their spacing is adjusted.

The method of testing includes:

mounting a semiconductor package in a tensiometer;

clamping a heat sink adhesively mounted to the semiconductor package;

securing the heat sink to a spindle of the tensiometer; and conducting a pulling test in the tensiometer.

These features provide not only a reliable technique for testing a particular combination of heat sink, package and adhesive, but also provides a reliable technique of choosing heat sink attach materials and assembly processes.

Other objects, features and advantages of the invention will become apparent in light of the following description thereof.

DETAILED DESCRIPTION OF THE INVENTION

Figure 1A:
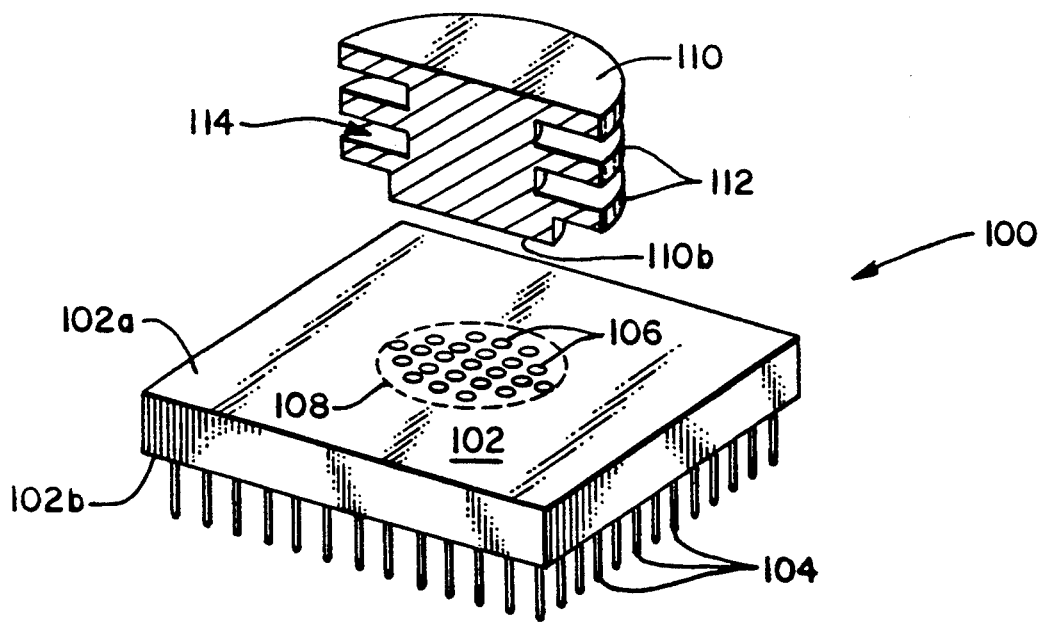
FIG. 1A is a partially perspective, partially in cross-section, exploded view of a heat sink and a semiconductor package, according to the prior art.
Figure 1B:
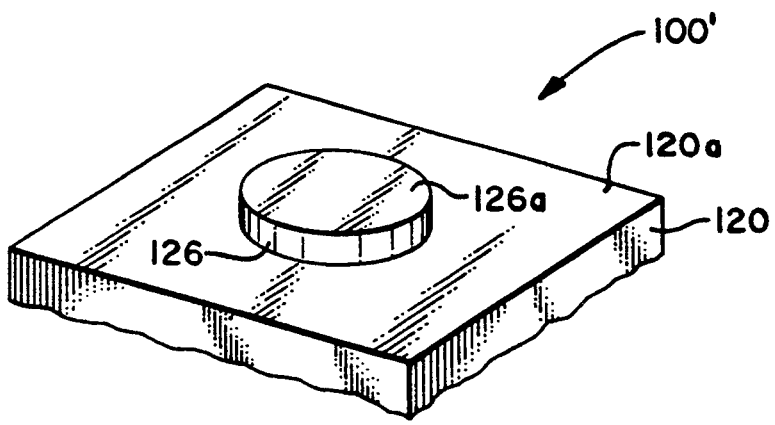
FIG. 1B is a perspective view of a partial semiconductor package body, according to the prior art.
Figure 2A:
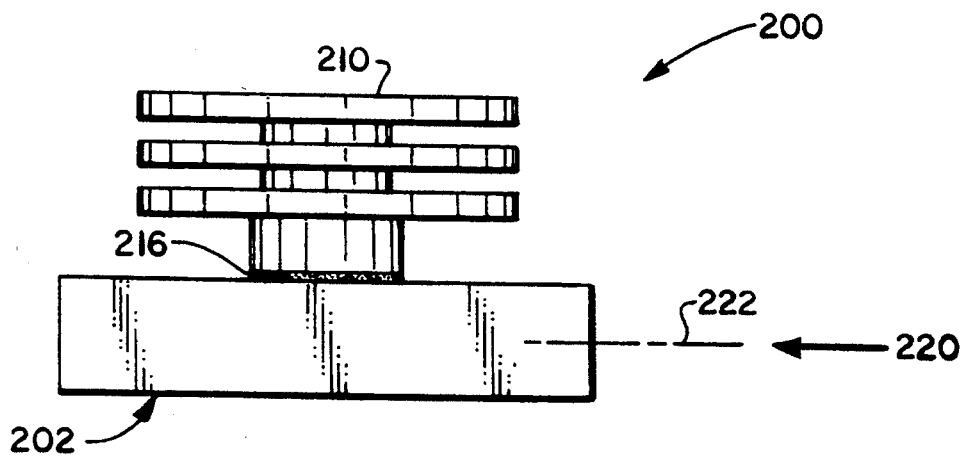
FIG. 2A is a side view of a heat sink mounted to a semiconductor package body, and a technique for testing the mounting integrity of the heat sink, according to the prior art.
Figure 2B:
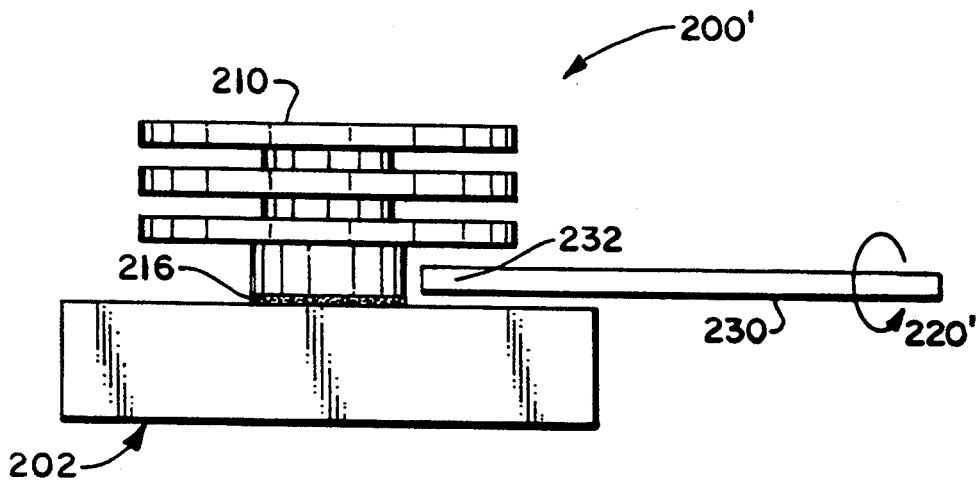
FIG. 2B is a side view of another technique for testing the mounting integrity of a heat sink, according to the prior art.

FIGS. 1A and 1B show semiconductor packages for mounting heat sinks, and have been described above. FIGS. 2A and 2B show techniques for testing the mounting integrity of heat sinks, and have been described above.

As mentioned above, what is needed is a reliable, safe, quantifiable technique for characterizing the mounting integrity of the adhesive bond between a heat sink and a semiconductor package body.

Figure 3:
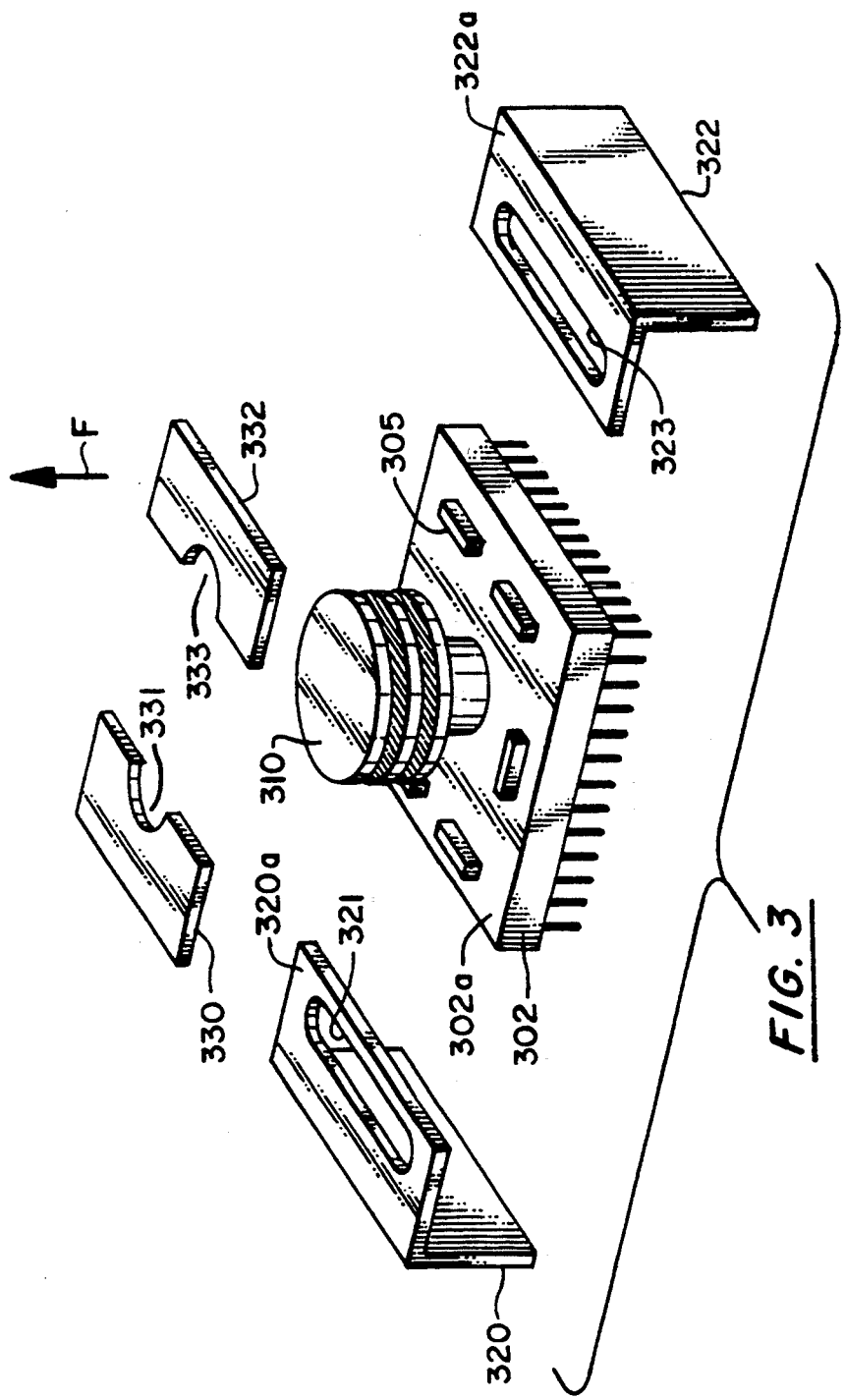
FIG. 3 is a generalized perspective view of the testing fixture and method of the present invention.

FIG. 3 illustrates, in principle, the testing technique of the present invention. Semiconductor package has a body 302, similar to the bodies 102, 120 or 202 described above. Additionally, chip capacitors 305 may be disposed on the top surface 302a of the body, as is known in the prior art. A heat sink 310 is mounted to the top surface of the body, in a manner described hereinabove.

Two "L"-shaped braces 320, 322 are provided. Each have a flat surface 320a, 322a for resting atop the top surface 302a of the package body 302. Elongated slots 321 and 323 are provided in the top surfaces 320a and 322a, respectively, for allowing chip capacitors 305 to pass freely through the flat surfaces 320a and 322a, to ensure direct, intimate contact between the braces and the package body. The braces 320, 322 are secured in a vise, or the like, to establish a fixed frame of reference for the package body. As discussed in greater detail hereinbelow, the braces are designed to be mounted to the base of a tensiometer, such as an INSTRON 4501.

Two flat jaws ("fixture platforms") 330, 332 are provided. Each jaw is essentially a flat plate, with a semicircular cutout 331 and 333 extending from an inner edge thereof. The jaws, and cutouts are sized and shaped to fit in the gap (see, e.g., 114, FIG. 1A) between adjacent fins on the heat sink, thereby "grasping the heat sink when they are brought together. The jaws can also grasp the heat sink under the bottommost fin, rather than between two adjacent fins. As described in greater detail hereinbelow, the jaws (and additional apparatus, described below) are designed to be secured to the pulling piston (spindle) of a tensiometer.

The mounting integrity of the adhesive bond between the heat sink and the package body is tested by:

1. mounting the package body to the base of a tensionmeter, using the braces 320, 322;
2. closing the jaws 330, 322 about the heat sink; and
3. applying a tensile pulling force, indicated at "F", to the heat sink.

By using a suitable, computer-controlled tensiometer (for example, the INSTRON 4501), the pulling force can be applied gradually, and a curve can be automatically plotted of the tensile strength of the adhesive bond between the heat sink and the package body. (This is akin to a traditional "stud pull" test.) This provides a true test of tensile strength, rather than the indirect indications of tensile strength provided by the prior art techniques (e.g., FIGS. 2A and 2B). Furthermore, once the package is mounted in the tensiometer, the test can proceed automatically, and at a safe distance from the operator. Furthermore, the results (e.g., the plotted curve) can be used to characterize the bonding process, and allow the designer to make more appropriate selections of parameters for the heat sink bonding process—namely, type and amount of adhesive, curing cycle, and the like. In this manner, a greatly improved technique for testing the mounting integrity of heat sinks to semiconductor packages is provided. This test can be terminated before destruction of the bond between the heat sink and the package. This is advantageous since it permits the tested heat sink and package to be later used and sold commercially.

Figure 4:
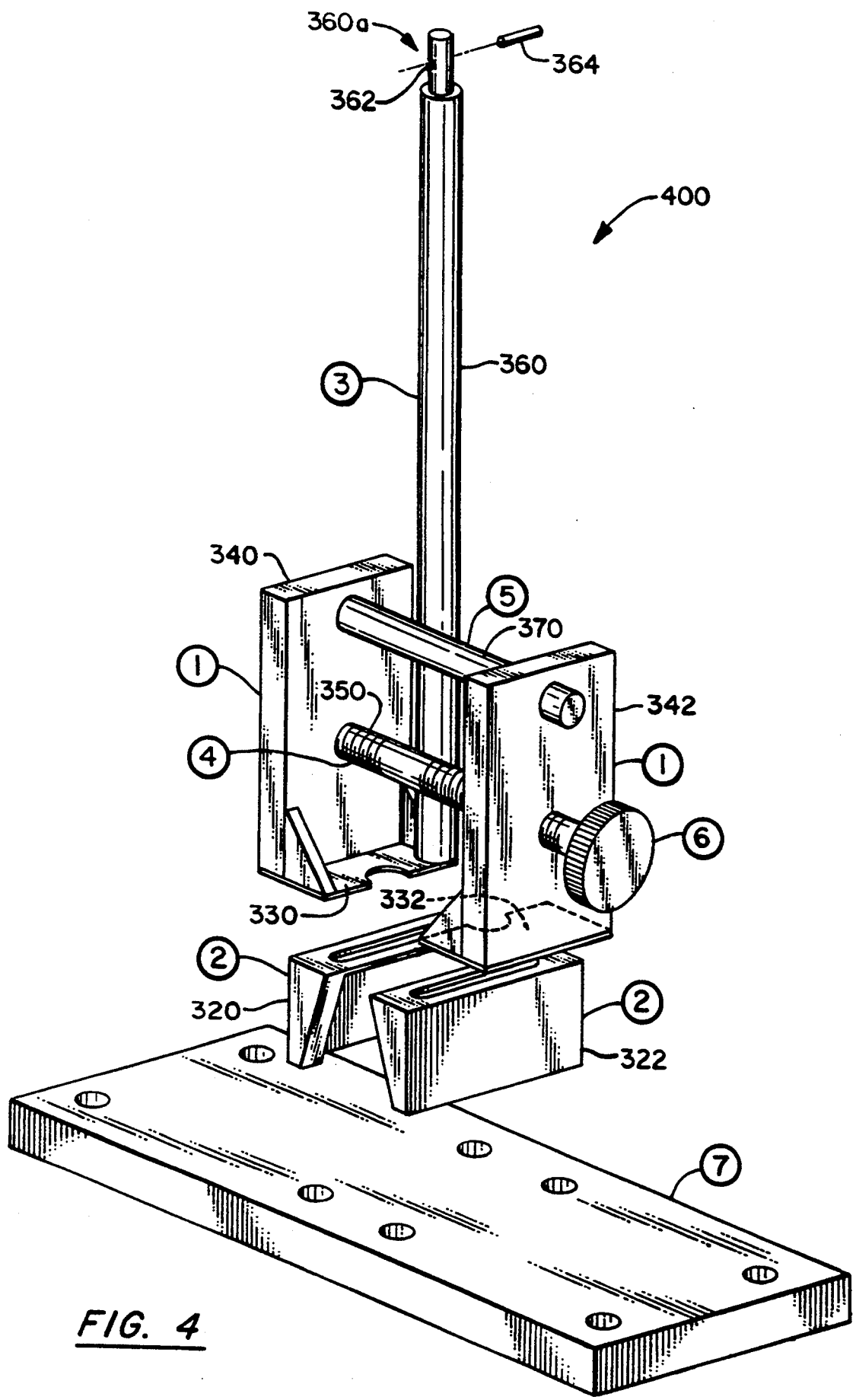
FIG. 4 is a more detailed perspective view of the testing fixture of the present invention.

FIG. 4 is a more detailed sketch of a test fixture 400 for performing the testing technique of the present invention, described above. The braces 320 and 322 (both labelled "2") are evident, as are the jaws 330 and 332. Element "7" is a mounting plate, to which the braces are secured (such as by screws), and which is ultimately secured to the base of the tensiometer.

The jaws 330 and 332 are mounted to blocks 340 and 342, respectively. These blocks ("1") are spaced apart, and their spacing is controlled by rotating a threaded shaft 350 ("4"; "6" is a knob at the end of the threaded shaft) that connects the two blocks together. The threaded shaft 350 also passes freely through a rod 360 ("3") which is oriented to apply a tensile force to the heat sink. The top (as viewed) end 360a of the rod 360 is provided with suitable means, such as a hole 362 for receiving a pin 364, for securing the rod 360 to the spindle (not shown) of the tensiometer (not shown).

In order to ensure that the blocks 340 and 342 remain parallel, a guide rod 370 ("5") is provided above (as viewed) the threaded shaft 350, and passes freely through the rod 360 and the blocks 340 and 342. Preferably, an additional guide rod (not shown) would be provided at a similar distance below (as viewed) the threaded shaft 350 to ensure that the blocks 340 and 342 remain parallel as they are adjusted inward (towards each other, for the jaws to grasp the heat sink) and outward (away from each other, to release the heat sink, or prior to grasping the heat sink).

The technique of using the apparatus of FIG. 4 is essentially similar to that described above with respect to FIG. 3, namely:

1. The fixture (400) is assembled to the tensiometer;
2. The specimen (semiconductor package) is clamped;
3. The jaws of the fixture 400 are opened wider than the heat sink by turning the knob at the end of the threaded shaft;
4. The fixture is moved down (by controlling the spindle position of the tensiometer) to a position where the jaws ("fixture platforms") are in line with a gap (space) between adjacent heat sink fins;
5. The jaws are closed about the heat sink; and
6. A programmed pulling test is initiated.

What is claimed is:

1. Method of testing the mounting integrity of a heat sink adhered to a surface of a semiconductor package, comprising:
    disposing two braces, each brace having a flat surface, on a surface of a semiconductor package body;
    inserting two jaws, each jaw having a semicircular cutout underneath a fin of a heat sink adhesively mounted to and extending from the surface of a the semiconductor package body;
    moving the jaws away from the braces with a force;
    measuring the force to determine a mounting integrity of the heat sink to the package body.

2. Method, according to claim 1, further comprising:
    the force is sufficient to cause the heat sink to separate from the semiconductor package body.

3. Method, according to claim 1, wherein:
    the jaws are inserted underneath a fin of the heat sink most proximate to the semiconductor package body.

4. Method, according to claim 1, wherein:
    the jaws are inserted between two adjacent fins of the heat sink.

5. Method, according to claim 1, further comprising:
    providing slots in alignment with chip capacitors mounted to the surface of the semiconductor package body.

6. Method, according to claim 1, further comprising:
    inserting the jaws underneath the fin of the heat sink from diametrically-opposed positions of the heat sink.

7. Fixture for testing the mounting integrity of a heat sink adhered to a semiconductor package, comprising:
    two braces, each having a flat surface for resting atop a top surface of a semiconductor package body;
    two flat, plate-like jaws, each having a semicircular cutout extending from an inner edge thereof, for fitting underneath a fin of a heat sink adhered to the top surface of the semiconductor package body; and
    means for moving the jaws away from braces via a force that is measured for testing the mounting integrity of the heat sink to the package.

8. Fixture, according to claim 7, wherein:
    the jaws fit between two adjacent fins of the heat sink.

9. Fixture, according to claim 7, further comprising:
    an elongated slot in each of the flat surfaces of the braces, for allowing chip capacitors mounted to the top surface of the semiconductor package to pass freely thorough the flat surfaces of the braces, thereby ensuring contact between the flat surfaces and the top surface of the semiconductor package body.

10. Fixture, according to claim 7, further comprising:
    two parallel, spaced-apart, blocks, each block associated with a respective jaw mounted to a respective one of the blocks;

a threaded shaft extending from the one block to the other block, and passing freely through the rod, for adjusting the spacing of the blocks.

11. Fixture, according to claim 10, further comprising:
   at least one guide rod extending from the one block to the other block, for ensuring that the blocks remain parallel when their spacing is adjusted.

* * * * *